United States Patent [19]

Quadranti et al.

[11] 4,272,281
[45] Jun. 9, 1981

[54] COMPOSITION FOR AND METHOD OF SELECTIVELY CONTROLLING WEEDS IN CEREALS

[75] Inventors: Marco Quadranti, Brugg; Willy Maurer, Basel; Kurt Maag, Muttenz, all of Switzerland

[73] Assignee: Ciba-Geigy Corporation, Ardsley, N.Y.

[21] Appl. No.: 56,669

[22] Filed: Jul. 11, 1979

[30] Foreign Application Priority Data

Jul. 20, 1978 [CH] Switzerland ................ 7837/78

[51] Int. Cl.³ .............. A01N 43/02; A01N 43/40
[52] U.S. Cl. ................................ 71/90; 71/94
[58] Field of Search ............................ 71/90, 94

[56] References Cited

U.S. PATENT DOCUMENTS

| | | | |
|---|---|---|---|
| 3,917,478 | 11/1975 | Moser et al. | 71/90 |
| 4,046,553 | 9/1977 | Takahashi et al. | 71/94 |
| 4,093,442 | 6/1978 | Schmidt et al. | 71/90 |
| 4,133,675 | 1/1979 | Schurter et al. | 546/302 |

Primary Examiner—Glennon H. Hollrah

Attorney, Agent, or Firm—Frederick H. Rabin

[57] ABSTRACT

The invention provides a herbicidal composition for the post-emergence selective control of grasses and weeds in cereals, such as wheat and barley. The composition contains two active components, one of which is N-(3-trifluoromethyl-1,2,4-thiadiazolyl-5)-N'-methyl-N'-methoxy urea and the other is a dichloropyridyloxy-α-phenoxypropionic acid derivative of the formula

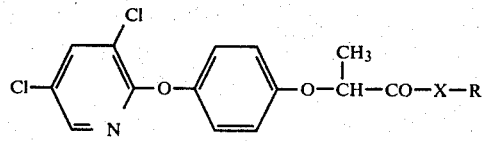

wherein X is oxygen or sulfur and R is hydrogen, a cation, a lower alkyl, alkenyl or alkynyl radical.

The invention also provides a post-emergence method of selectively controlling grasses and weeds in crops of cereals, such as wheat and barley, which comprises the use of this composition. In particular wild oat species are selectively controlled.

4 Claims, No Drawings

COMPOSITION FOR AND METHOD OF SELECTIVELY CONTROLLING WEEDS IN CEREALS

The present invention provides a novel herbicidal composition having unexpected herbicidal properties that is exceptionally suited for the post-emergence selective control of weeds in cereals such as wheat, in particular for the control of both resistant monocotyledonous harmful grasses and dicotyledonous weeds, and a method of selectively controlling weeds in cereal crops.

Herbicidal compounds of the series of halopyridyloxy-α-phenoxypropionic (and -thiopropionic) acid derivatives, for example α-[4-(3′,5′-dichloropyridyl-2′-oxy)-phenoxy]-propionic acid and the methyl ester thereof, as well as other esters disclosed in U.S. Pat. No. 4,046,553, are distinguished in post-emergence application by an exceptionally potent action against grasses occurring in cereals, for example against the following very harmful grasses: Avena fatua, Avena sterilis, Alopecurus myosuroides, Lolium perenne, Phalaris ssp., Bromus tectorum, Setaria ssp. The efficacious action of these compounds also occurs under field conditions at rates of application of 500 g of active substance per hectare and less.

Unfortunately, compounds of this type cannot be used as selective post-emergence herbicides despite their good action, as the simultaneous damage caused to cereal species, such as wheat, barley and rice, is too great.

As disclosed in applicants' pending U.S. Pat. application Ser. No. 2,923, this problem can be solved in certain cases, especially where the cultivated plants are wheat and barley, by using the unsaturated propionic and thiopropionic acid esters described in that application instead of the α-[4-(3′,5′-dichloropyridyl-2′-oxy)-phenoxy]-propionic acid or the methyl ester thereof, or other simple esters of U.S. Pat. No. 4,046,553.

Where there is strong infestation by monocotyledonous weeds, it is however sometimes desirable when using these unsaturated esters to exceed the concentrations which are still not phytotoxic to wheat. On such occasions, these compounds too can also damage the cereal.

On the other hand, a heterocyclic urea derivative, N-(3-trifluoromethyl-1,2,4-thiadiazolyl-5)-N′-methyl-N′-methoxy urea of the formula I

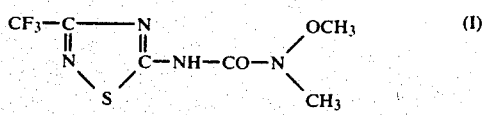

known, inter alia, from U.S. Pat. No. 3,917,478 and German Offenlegungsschrift No. 2,113,033, has an excellent post-emergence action against dicotyledonous weeds such as Galium ap., Veronica ssp., Viola tricolor, Polygonum ssp., Papaver rhoas and others. However, the good action of this urea compound is limited to dicotyledonous weeds and it has only little effect on the grasses mentioned previously.

The present invention is based on the completely surprising observation that a combination of this heterocyclic urea of the formula I above with a lower saturated or unsaturated ester of a halogenated pyridyloxy-α-phenoxypropionic or -thiopropionic acid of the formula II

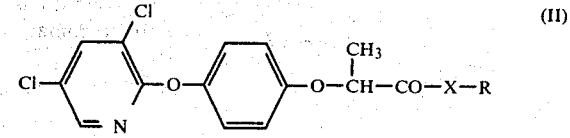

wherein X is oxygen or sulfur and R is hydrogen, a cation, a lower alkyl, alkenyl or alkynyl radical, exhibits not merely the expected additive action of the individual components, but completely neutralises the harmful action of component of formula II on cereals such as wheat and barley, i.e. the urea component I antagonises the harmful action of the component II on e.g. wheat by acting as a safener. The combination of the invention, however, exhibits no loss of potency against troublesome grasses and dicotyledonous weeds.

Both components I and II thus combine additively to form a herbicide with broad activity spectrum whilst simultaneously neutralising the phytotoxicity of component II to wheat and other cereal species. This affords the possibility of using the mixture of both components as a post-emergence herbicide with broad activity spectrum against the most important mono- and dicotyledonous weeds occurring in wheat and other species of cereals.

It is possible, for example, to control the following weeds in winter, summer and hard wheat:

monocots: Avena fatua, Avena sterilis, Alopecurus myosuroides, Lolium perenne, Phalaris ssp., Bromus tectorum, Setaria ssp., Apera, Avena ludoviciana etc.

dicots: Stellaria, Papaver, Matricaria, Sinapis, Galeopsis, Chrysanthemum, Veronica, Lamium, Polygonum, Capsella, Galium ap., Viola tricolor, Amaranthus, Chenopodium etc.

A preferred compound of the formula II is α-[4-(3′,5′-dichloropyridyl-2′-oxy)-phenoxy]-propionic acid methyl ester of the formula IIa

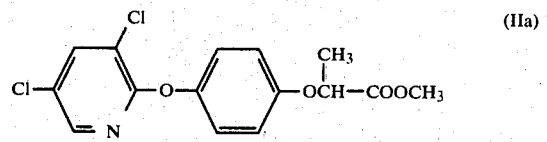

in both its racemic (±)-form and its optically active R(+) form with more potent herbicidal action.

The optically more active enantiomers and unsaturated esters of propionic and thiopropionic esters of the formula II also constitute the subject matter of pending patent applications, in so far as they are not known from U.S. Pat. No. 4,046,553 and Japanese patent publication No. 1,142,537.

The mixture ratio of component I to component II in the composition of this invention is not especially critical and can vary between 1:10 and 10:1. Preferred mixtures are those containing about equal amounts of both components (1:1) and those wherein there is a slightly larger amount of one component. Preferably in that case there shall be a larger amount of urea component I, e.g. the ratio of component I to component II is 3:2 or 4:3, and even 4:1 to 5:1.

The total rate of application of both compounds together is preferably 0.25 to 5 kg per hectare; but the amount of urea component I shall then, as far as possible, not exceed 4 kg/ha and the amount of component II shall not be more than 1 kg/ha.

When the composition of the present invention is used in such a concentration range virtually no damage to the cereal crops can be observed, whereas troublesome grasses and weeds wither almost totally at low concentrations.

This invention also relates to the use of the composition of the invention, that is to say, to a post-emergence method of selectively controlling troublesome grasses and weeds in cereals.

The active substance mixture of this invention effects almost total destruction of most weeds and troublesome grasses at low rates of application of 0.5 to 1 kg/ha, whilst even at high rates of application of 4 and 5 kg/ha only insignificant damage to wheat and barley is observed. Different types of the problem weed Avena fatua (wild oat) are totally destroyed at all rates of application employed in practice.

The active substance combination also achieves a high degree of weed control where both single compounds become ineffective at too low rates of application. The consequence is a substantial broadening of the activity spectrum against weeds and a considerable increase in the safety margin in cereal crops, which is necessary and desirable in the event of unintentional overapplication.

The composition of the invention containing the novel active substance combination additionally contains suitable carriers and/or other adjuvants. Suitable carriers and adjuvants can be solid or liquid and correspond to the substances ordinarily employed in the art of formulation, for example natural or regenerated mineral substances, solvents, dispersants, wetting agents, tackifiers, thickeners, binders or also fertilisers.

The content of active substance in commercial compositions is between 0.1 and 95, preferably between 1 and 80, percent by weight.

For application, the active substance combination can be processed to the following liquid formulations (the percentages by weight in brackets denote advantageous amounts of active substance):

(a) active substance concentrates which are dispersible in water:
   wettable powders and pastes (25–90% in commercial packs, 0.01 to 15% in ready for use solution);
   emulsifiable concentrates and concentrated solutions (10 to 50%; 0.01 to 15% in ready for use solution);
(b) solutions (0.01 to 20%).

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foams and, optionally, solvents.

Wettable powders and pastes are obtained by mixing and grinding the active substances with dispersing agents and pulverulent carriers in suitable devices until homogeneity is attained. Suitable carriers are, for example, those already mentioned for the solid forms of application. In some cases it is advantageous to use mixtures of different carriers. As dispersing agents there can be used, for example, condensation products of sulfonated naphthalene and of sulfonated naphthalene derivatives with formaldehyde, condensation products of naphthalene or naphthalene sulfonic acids with phenol and formaldehyde, as well as alkali metal, ammonium and alkaline earth metal salts of ligninsulfonic acid, in addition, alkylarysulfonates, alkali metal and alkaline earth metal salts of dibutynaphthalene-sulfonic acid, fatty alcohol sulfates, such as salts of sulfated hexadecanols, heptadecanols, octadecanols, and salts of sulfated fatty alcohol glycol ethers, the sodium salt of oleylmethyltauride, dialkyldilaurylammonium chloride and fatty acid alkali metal and alkaline earth metal salts.

Suitable anti-foams are silicones. The active substances are so mixed, ground sieved and strained with the additives mentioned above that, in wettable powders, a solid particle size of 0.02 to 0.04 mm and in pastes, of 0.03 mm, is usually not exceeded. Emulsifiable concentrates and pastes are formulated by using dispersing agents, such as those cited previously above, organic solvents, and water. Examples of suitable solvents are: alcohols, xylenes, toluene, dimethyl sulfoxide, N,N-dialkylated amides and trialkylamines. The solvents must be practically odourless, not phytotoxic, inert to the active substances, and not readily combustible.

Furthermore, the compositions of the invention can be applied in the form of solutions. For this purpose both active substances I and II are dissolved in suitable organic solvents, mixtures of solvents, water, or mixtures of organic solvents and water. Aliphatic and aromatic hydrocarbons, chlorinated derivatives thereof or alkylnaphthalenes can be used as organic solvents.

The compositions of the present invention can be mixed with other biocidal active substances or compositions, e.g. insecticides, acaricides, fungicides, bactericides, growth regulators, rodenticides or nematocides, in order to broaden the activity spectrum.

The compositions of the invention can additionally contain plant fertilisers, trace elements and other substances which promote plant cultivation. It will be readily understood that compositions are also possible which, in addition to component I, also contain several representatives of component II.

The following Examples will serve to illustrate in more detail the preparation of solid and liquid formulations containing the compounds of the invention. Throughout, parts and percentages are by weight.

Wettable Powders: The following constituents are used for formulate (a) a 70% and (b) a 25% wettable powder:

(a)

42 parts of a the urea of the formula I,
28 parts of 4-[3',5'-dichloropyridyl-2'-oxy)-α-phenoxy]-propionic acid methyl ester of the formula IIa
5 parts of sodium dibutylnaphthalenesulfate,
3 parts of naphthalenesulfonic acid/phenolusulfonic acid/formaldehyde condensate (3:2:1),
10 parts of kaolin,
12 parts of Champagne chalk;

(b)

15 parts of the urea of the formula I,
10 parts of 4-[3',5'-dichloropyridyl-2'-oxy)-α-phenoxy]-propionic acid methyl ester of the formula IIa,
5 parts of sodium oleylmethyltauride
2.5 parts of naphthalenesulfonic acid/formaldehyde condensate,
0.5 part of carboxymethyl cellulose,
5 parts of neutral potassium aluminium silicate,
62 parts of kaolin.

The active substances and adjuvants are applied to kaolin and chalk and then mixed and ground, to produce wettable powders of excellent wettability and suspension power. By diluting these wettable powders with water it is possible to obtain suspensions of the desired concentration. These suspensions can be used for the post-emergence control of weeds and troublesome grasses in cereal crops.

Paste: The following substances are used to formulate a 45% paste:

30 parts of the active substance of the formula I,
15 parts of an active substance of the formula II,
5 parts of sodium aluminium silicate,
14 parts of cetyl polyethylene glycol ether with 8 moles of ethylene oxide,
1 part of oleyl polyethylene glycol ether with 5 moles of ethylene oxide,
2 parts of spindle oil,
10 parts of polyethylene glycol.

The active substances are homogenised with the adjuvants in appropriate devices and ground. By diluting the resulting paste with water, it is possible to prepare suspensions having the desired concentration of active substance.

Emulsifiable Concentrate: The following ingredients are mixed to formulate a 25% emulsion concentrate:

25 parts of an active substance mixture (2:1)
5 parts of a mixture of nonylphenolpolyoxyethylene and calcium dodecylbenzenesulfonate,
35 parts of 3,5,5-trimethyl-2-cyclohexen-1-one.
15 parts of dimethyl formamide,
20 parts of xylene.

This concentrate can be diluted with water to give emulsions of suitable concentrations.

The active substance combination can be employed in one of the conventional formulations in the customary manner, for example by dusting, spraying, drenching, pouring or scattering.

The tests described hereinafter illustrate the outstanding suitability of the novel active substance combination for the selective control of mono- and dicotyledonous weeds in wheat and barley while simultaneously causing no damage to these plants.

The components are tested singly and in combination on normal arable land in a field of wheat or barley that is strongly infested with grasses. The concentrations and mixture ratios, the species of cultivated plant and weed, and the location and time of treatment and evaluation of the tests are stated at the beginning of each table.

Treatment was by the post-emergence method. The amount of spray employed of the different active substances and their mixtures of varying total concentration was in each case 500 liters per hectare. The sprays are obtained from wettable powders (e.g. 80%) or from emulsifiable concentrates (e.g. 25%) by dilution with water.

Each of the parcels of land treated with a spray of specific concentration had an area of 4 cm².

The urea component was N-(3-trifluoromethyl-1,2,4-thiadiazolyl-5-)-N'-methoxy-N'-methyl urea of formula I. The pyridyloxyphenoxypropionic acid derivative was 4-[3',5'-dichloropyridyl-2'-oxy]-α-phenoxypropionic acid methyl ester of the formula IIa.

Test 1

Test location: Sousay, France

Cultivated plant: winter wheat of the "Top" variety

Weeds: *Avena fatua; Veronica hederifolia Galium aparine*

Time of treatment: Mid-March 1978 when the wheat was in the middle of tillering, *Avena fatua* was starting to tiller, *Veronica* was in the 3- to 4- leaf stage and Galium was in the 4 *rosette* stage.

Evaluation of the test: 75 days after treatment.

Test results

| Product (kg/ha) | | | Damage in % | | | |
|---|---|---|---|---|---|---|
| I | IIa | Total | Wheat | Avena fatua | Veron hed. | Galium ap. |
| 0.5 | — | | 0 | 0 | 0 | 90 |
| 0.75 | — | | 0 | 0 | 20 | 90 |
| 1.0 | — | | 0 | 0 | 30 | 90 |
| 1.25 | — | | 0 | 0 | 40 | 90 |
| 1.5 | — | | 0 | 0 | 50 | 95 |
| 1.75 | — | | 0 | 20 | 80 | 95 |
| — | 0.5 | | 40 | 100 | 0 | 0 |
| — | 0.75 | | 85 | 100 | 0 | 0 |
| — | 1.0 | | 95 | 100 | 0 | 0 |
| — | 1.25 | | 95 | 100 | 0 | 0 |
| — | 1.5 | | 98 | 100 | 0 | 0 |
| — | 1.75 | | 100 | 100 | 0 | 0 |
| 0.5 | 0.5 | 1.0 | 0 | 98 | 75 | 88 |
| 0.75 | 0.5 | 1.25 | 0 | 98 | 88 | 90 |
| 1.0 | 0.5 | 1.5 | 0 | 98 | 90 | 90 |
| 0.75 | 0.75 | 1.5 | 0 | 99 | 90 | 90 |
| 1.0 | 0.75 | 1.75 | 0 | 100 | 92 | 92 |

Test 2

Test location: Canton Geneva, Switzerland

Cultivated plant: winter wheat of the "Zenith" variety

Weed: *Avena fatua*

Time of treatment: Beginning of April 1978 when the wheat and *Avena fatua* were in the middle of tillering.

Evaluation of the test: 35 days after treatment.

Results:

| Product (kg/ha) | | | Damage in % | |
|---|---|---|---|---|
| I | IIa | Total | Wheat | Avena fatua |
| 0.5 | — | | 0 | 0 |
| 0.75 | — | | 0 | 0 |
| 1.0 | — | | 0 | 0 |
| 1.25 | — | | 0 | 5 |
| 1.5 | — | | 0 | 5 |
| 1.75 | — | | 0 | 5 |
| — | 0.5 | | 50 | 85 |
| — | 0.75 | | 65 | 96 |
| — | 1.0 | | 70 | 98 |
| — | 1.25 | | 75 | 98 |
| — | 1.5 | | 80 | 99 |
| — | 1.75 | | 85 | 99 |
| 0.5 | 0.5 | 1.0 | 5 | 80 |
| 0.75 | 0.5 | 1.25 | 5 | 85 |
| 1.0 | 0.5 | 1.5 | 10 | 95 |
| 0.75 | 0.75 | 1.5 | 10 | 95 |
| 1.0 | 0.75 | 1.75 | 10 | 95 |

Test 3
Test location: Lerida, Spain
Cultivated plant: winter wheat of the "Capitole" variety
Weeds: Avena ludoviciana, Lolium rigidum, Papaver rh., Veronica hed.
Time of treatment: End of February 1978 when the wheat was starting to tiller or was in the middle or tillering, Avena lud. was starting to tiller, Lolium was starting to tiller or was in the middle of tillering, Papaver was in the 8-9-leaf stage and Veronica was in the 4-leaf stage.
Evaluation of the test: 53 days after treatment.
Results:

| Product (kg/ha) | | | Damage in % | | | | |
|---|---|---|---|---|---|---|---|
| I | IIa | Total | Wheat | Av. lud. | Lol. rig. | Papaver | Veronica |
| 0.5 | — | | 0 | 0 | 0 | 40 | 40 |
| 0.75 | — | | 0 | 10 | 10 | 100 | 70 |
| 1.0 | — | | 0 | 20 | 40 | 100 | 95 |
| 1.25 | — | | 0 | 30 | 40 | 100 | 95 |
| 1.5 | — | | 0 | 40 | 40 | 100 | 95 |
| 1.75 | — | | 0 | 40 | 70 | 100 | 100 |
| — | 0.5 | | 60 | 100 | 100 | 0 | 0 |
| — | 0.75 | | 60 | 100 | 100 | 0 | 0 |
| — | 1.0 | | 80 | 100 | 100 | 0 | 0 |
| — | 1.25 | | 80 | 100 | 100 | 0 | 0 |
| — | 0.5 | | 80 | 100 | 100 | 0 | 0 |
| — | 1.75 | | 80 | 100 | 100 | 0 | 0 |
| 0.5 | 0.5 | 1.0 | 7 | 100 | 100 | 95 | 95 |
| 0.75 | 0.5 | 1.25 | 0 | 100 | 100 | 92 | 92 |
| 1.0 | 0.5 | 1.5 | 2 | 98 | 100 | 100 | 95 |
| 0.75 | 0.75 | 1.5 | 4 | 100 | 100 | 100 | 98 |
| 1.0 | 0.75 | 1.75 | 12 | 100 | 100 | 100 | 98 |

Test 4
Test location: Möhlin, Canton Aargau, Switzerland
Cultivated plant: summer wheat of the "Tano" variety
Weeds: Avena ssp., Amaranthus retroflexus, Chenpodium album
Time of treatment: Middle of June 1978 when the wheat and Avena fatua were starting to tiller and the dicotyledonous weeds had formed some leaves.
Evaluation of the test: 26 days after treatment.
Results:

| Product (kg/ha) | | | Damage in % | | | |
|---|---|---|---|---|---|---|
| I | IIa | Total | Wheat | Avena ssp. | Amar. ret. | Chenop. alb. |
| 0.5 | — | | 0 | 0 | 100 | 100 |
| 0.75 | — | | 0 | 0 | 100 | 100 |
| 1.5 | — | | 0 | 0 | 100 | 100 |
| — | 0.25 | | 95 | 100 | 100 | 100 |
| — | 0.5 | | 98 | 100 | 100 | 100 |
| — | 0.75 | | 100 | 100 | 100 | 100 |
| — | 1.5 | | 100 | 100 | 100 | 100 |
| 0.5 | 0.25 | 0.75 (2:1) | 20 | 100 | 100 | 100 |
| 1.25 | 0.25 | 1.5 (5:1) | 15 | 100 | 100 | 100 |

Test 5
In this test the propargyl ester of α-[4-(3',5'-dichloropyridyl-2'-oxy)-phenoxythiopropionic acid of the formula IIb

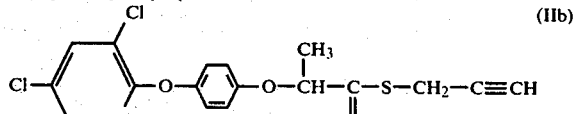

(IIb)

was used instead of the halopyridyloxyphenoxypropionic acid component of the formula IIa.

Test location: Blansingen, West Germany
Cultivated plant: summer barley of the "Carina" variety
Weeds: Avena fatua and Alopecurus
Time of treatment: End of May 1978 when barley and Alopecurus had finished tillering and were starting to shoot.
Evaluation of test: 44 days after treatment.
Results

| Product (kg/ha) | | | Damage in % | | |
|---|---|---|---|---|---|
| I | IIb | Total | Barley | Avena fatua | Alopecurus |
| 0.5 | — | | 0 | 0 | 0 |
| 0.75 | — | | 0 | 0 | 0 |
| 1.0 | — | | 0 | 0 | 0 |
| 1.25 | — | | 5 | 0 | 0 |
| 1.5 | — | | 20 | 0 | 10 |
| — | 0.25 | | 20 | 55 | 90 |
| — | 0.05 | | 35 | 90 | 90 |
| — | 0.75 | | 80 | 99 | 95 |
| — | 1.0 | | 97 | 100 | 100 |
| — | 1.25 | | 97 | 100 | 100 |
| — | 1.5 | | 99 | 100 | 100 |
| 0.5 | 0.25 | 0.75 (2:1) | 0 | 30 | 30 |
| 0.75 | 0.25 | 1.0 (3:1) | 5 | 98 | 90 |
| 1.0 | 0.25 | 1.25 (4:1) | 10 | 99 | 95 |
| 0.5 | 0.5 | 1.0 (1:1) | 10 | 100 | 98 |
| 0.75 | 0.5 | 1.25 (3:2) | 15 | 100 | 98 |
| 1.0 | 0.5 | 1.5 (2:1) | 20 | 100 | 98 |

These tests demonstrate clearly that the phytotoxicity of the mixture to wheat and barley is substantially lower than when the monocot composition IIa or IIb is used by itself in the amount of the mixture, without any loss of activity against the grasses and weeds. Similar effects have also been observed between urea component I and other active substances of the formula II.

Further possible active substances of the formula II are: the free acid corresponding to compound IIa and its salts, the ethyl, propyl, butyl, allyl, methallyl and propargyl ester of this acid and the same salts and esters of the corresponding thiopropionic acid, wherein X in formula II is a sulfur atom.

What is claimed is:

1. A herbicidal composition for the selective control of weeds in wheat crops which comprises a herbicidally effective amount of two active components, one component being N-(3-trifluoromethyl-1,2,4-thiadiazolyl-5)-N'-methyl-N'-methoxyurea and the other component being methyl α-[4-(3',5'-dichloropyridyl-2'-oxy)-phenoxy]-propionate, together with inert carriers and or other inert adjuvants, in which the ratio of the urea component to the methyl propionate component is from 1:1 to 5:1.

2. A herbicidal composition for the selective control of weeds in wheat and barley crops which comprises a herbicidally effective amount of two active components, one component being N-(3-trifluoromethyl-1,2,4-thiadiazolyl-5)-N'-methyl-N'-methoxyurea and the other component being propargyl α-[4-(3',5'-dichloropyridyl-2'-oxy)-phenoxy]-thiopropionate, together with inert carriers and or other inert adjuvants, in which the ratio or the urea component to the propargyl thiopropionate component is from 1:1 to 4:1.

3. A post-emergence method for selectively controlling weeds in wheat crops which comprises applying to said crops a herbicidally effective amount of the composition according to claim 1.

4. A post-emergence method of selectively controlling weeds in wheat and barley crops which comprises applying to said crops a herbicidally effective amount of the composition according to claim 2.

* * * * *